United States Patent
Mueller et al.

(10) Patent No.: US 9,410,925 B2
(45) Date of Patent: Aug. 9, 2016

(54) CAPILLARY TUBES FOR ELECTROPHORESIS

(75) Inventors: Dominik Mueller, Karlsruhe (DE); Karsten Pinkwart, Pfinztal (DE); Jens Tuebke, Waldbronn (DE)

(73) Assignee: FRAUNHOFER-GESELLSCHAFT ZUR FORDERUNG DER ANGEWANDTEN FORSCHUNG E.V. (DE)

( * ) Notice: Subject to any disclaimer, the term of this patent is extended or adjusted under 35 U.S.C. 154(b) by 478 days.

(21) Appl. No.: 13/876,006

(22) PCT Filed: Sep. 23, 2011

(86) PCT No.: PCT/EP2011/066551
§ 371 (c)(1),
(2), (4) Date: Oct. 24, 2013

(87) PCT Pub. No.: WO2012/041767
PCT Pub. Date: Apr. 5, 2012

(65) Prior Publication Data
US 2014/0034496 A1    Feb. 6, 2014

(30) Foreign Application Priority Data
Sep. 27, 2010  (DE) .......................... 10 2010 041 433

(51) Int. Cl.
G01N 27/447  (2006.01)
G01N 27/453  (2006.01)

(52) U.S. Cl.
CPC .... *G01N 27/44791* (2013.01); *G01N 27/44713* (2013.01); *G01N 2223/628* (2013.01)

(58) Field of Classification Search
CPC ................... G01N 27/44795; G01N 2223/628
See application file for complete search history.

(56) References Cited

U.S. PATENT DOCUMENTS

| | | | |
|---|---|---|---|
| 4,908,116 A | 3/1990 | Zare et al. | |
| 5,217,590 A * | 6/1993 | Lauer et al. | 204/453 |
| 5,223,114 A | 6/1993 | Zare et al. | |
| 5,298,134 A | 3/1994 | Zare et al. | |
| 5,409,586 A * | 4/1995 | Kamahori et al. | 204/452 |
| 5,582,705 A * | 12/1996 | Yeung et al. | 204/603 |
| 6,676,819 B1 * | 1/2004 | Liu et al. | 204/451 |
| 6,863,790 B1 | 3/2005 | Moini et al. | |

FOREIGN PATENT DOCUMENTS

| | | |
|---|---|---|
| EP | 0295942 A2 | 12/1988 |
| EP | 0401033 A2 | 12/1990 |

(Continued)

OTHER PUBLICATIONS

JPO computer-generated English language translation of Yukimasa Go JP 2007-078429 A, patent published Mar. 29, 2007.*

(Continued)

*Primary Examiner* — Alexander Noguerola
(74) *Attorney, Agent, or Firm* — Tarolli, Sundheim, Covell & Tummino LLP

(57) ABSTRACT

The present invention relates to a plastic capillary tube for capillary electrophoresis, in which the plastic capillary tube has an inlet opening and an outlet opening and, furthermore, has at least one hole in the capillary tube wall and the diameter of the hole on the inside of the capillary tube wall $d_{L(innen)}$ lies in the range from 0.5 µm to 30 µm.

11 Claims, 1 Drawing Sheet

(56) References Cited

FOREIGN PATENT DOCUMENTS

| JP | 1158342 | A | | 6/1989 | |
|---|---|---|---|---|---|
| JP | 06-050938 | | | 2/1994 | |
| JP | 200740816 | A | | 2/2007 | |
| JP | 2007-078429 | A | * | 3/2007 | ............ G01N 27/447 |
| JP | 2008214244 | A | | 10/2008 | |
| WO | 2009118775 | A1 | | 10/2009 | |

OTHER PUBLICATIONS

JPO computer-generated English language translation of JP 6-50938 A. patent published Feb. 25, 1994.*
Korean Office Action dated Jul. 31, 2014.
German Office Action dated Sep. 5, 2011.
Hancu et al: "Separation of 1,4-benzodiazepines by micellar elektrokinetic capillary chromatography" Journal of Biochemical and Biophysical Methods, Amsterdam, NL, vol. 69, No. 3, Jan. 10 2007, pp. 251-259.
Osbourn D M et al: "Cellulose Acetate Decoupler for on-Column Electrochemical Detection in Capillary Electrophoresis", Analytical Chemistry, American Chemical Society, US, vol. 73, No. 24, Dec. 15, 2001, pp. 5961-5964.
Arnett et al: "Determination of 8-oxoguanine and 8-hydroxy-2'-deoxyguanosine in the rat cerebral cortex using microdialysis sampling and capillary electrophoresis with electrochemical detection", Journal of Chromatography B: Biomedical Sciences & Applications, Elsevier, Amsterdam, NL, vol. 827, No. 1, Nov. 5, 2005, pp. 16-25.
Rossier, Joel S., et al. Electrophoresis with electrochemical detection in a polymer microdevice, Journal of Electroanalytical Chemistry, vol. 492 (2000), 15-22.
English Abstract of JP20080241244A and JP2007-040816A.
Japanese Office Action (English Translation), mailed Jan. 27, 2014.

* cited by examiner

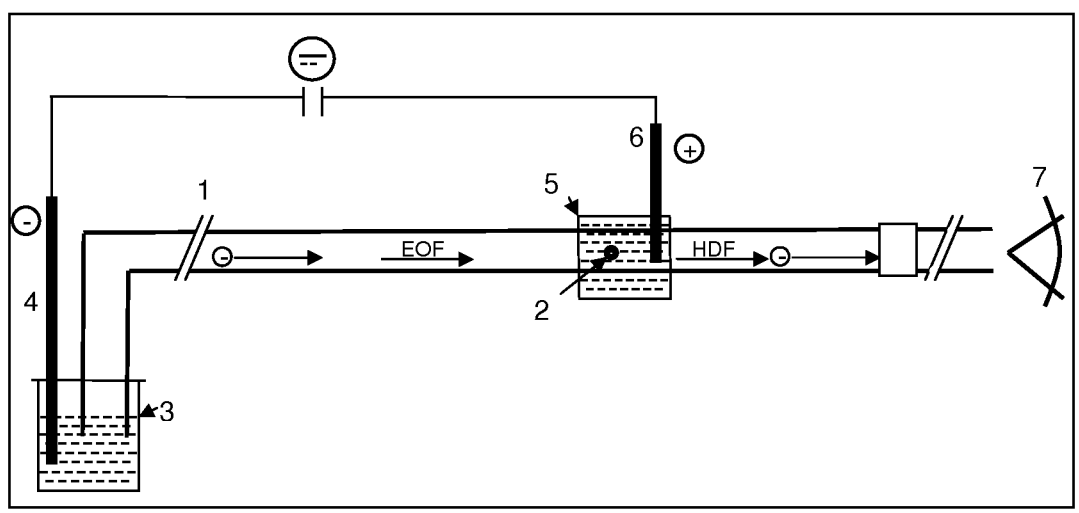

CAPILLARY TUBES FOR ELECTROPHORESIS

RELATED APPLICATION

This application is a National Phase filing of PCT/EP2011/066551, filed Sep. 23, 2011, and claims priority to German Application No. 102010041433.6, filed Sep. 27, 2010, the subject matter of which are incorporated herein by reference in their entirety.

FIELD OF THE INVENTION

The present invention relates to a capillary for capillary electrophoresis, and to a chemical separation and analysis device which includes said capillary.

BACKGROUND

Electrophoretic separation is caused by application of a voltage. Charged particles migrate in the electric field to the corresponding poles, for example negatively charged particles to the positive pole. In this process, each charged particle exhibits different speeds in the electric field because of different mobilities. The mobility depends on the charge number and on the radius of the particle and on the hydrate layer forming on the particle. The viscosity of the buffer likewise impairs the mobility of the charged particles. Charged particles with different mobility constants can therefore be separated from one another.

A further electrophoretic effect which influences the separation in the electric field is the electroosmotic flow (EOF). Said uniform and directional flow is generated by surface charges on the inner capillary surface. Capillary materials with a high charge density generate a high EOF. A negative surface such as is formed in the case of glass, for example, produces a flow in the direction of the positive pole. The EOF accelerates negatively charged particles and brakes positively charged particles. Neutral particles, by contrast, migrate through the capillary with the EOF. The pH has a significant influence on the surface charge, and therefore likewise on the EOF.

Glass capillaries are routinely used, since they can be produced simply and cost-effectively. A further great advantage is the optical transparency to light in the UV/VIS region. Optical detectors can therefore be used on-column without coming into contact with the liquid subjected to voltage. However, it is only compounds which absorb in the appropriate wavelength region which can be detected. Thus, for example, monosaccharides and oligosaccharides have no chromophore. Other sensitive detectors such as mass-selective and electrochemical detectors must be used for these compounds. However, said detectors come into contact with the liquid subjected to voltage, which leads to a significant deterioration or to the failure of these detectors. There is thus a mandatory requirement to remove the voltage from the separation section before the fluid reaches the detector.

A further disadvantage of glass capillaries is the high adsorption tendency of compounds which can agglomerate irreversibly on the negative surface. An inertization of the inner surface can be brought about by a thin coating with a polymer. However, the intensive UV radiation of the detector can easily irreversibly damage the fine polymer layer.

To date, the problem of downstream detection has been solved by a so-called "sheath interface", for example. After the electrophoretic separation, the fluid passes to the mass spectrometer via an interface. A liquid (sheath liquid) is fed in the interface in order to be able to remove the voltage from the capillary. An undesired effect of the feed is the dilution with the fluid from the capillary. This substantially reduces the detection sensitivity.

In order not to worsen the detection sensitivity in the downstream detection, attempts have been made in recent developments to dispense with the sheath liquid and, instead, to use a so-called "sheathless interface". Novel developments are described by Zamfir et al. in *Journal of Chromatography A*, 1159 (2007), 2-13. Conductive so-called emitters consist of a specifically produced glass capillary and a conductive material which is applied to the outside of the glass capillary. The emitter is then connected to the separation capillary and electrical contact is established. The requirements placed on the design and material of the emitter are very stringent for the purpose of obtaining an excellent and reproducible spray characteristic for mass spectrometry. Furthermore, the emitter must not have a negative influence on the separation quality and thus on the analytical performance. The design has the advantage that the emitter can be applied flexibly to various separation columns, although separation capillary and emitter must be cleanly connected to one another. According to the publication, however, there are difficulties in implementing said requirements.

In a workshop for capillary electrophoresis which was held by Beckman/Coulter and took place in September 2009 in Basel, a newly-developed emitter was presented. In this case, the last 4 cm of a glass capillary are etched at one end until the wall of the glass capillary becomes porous and the voltage can thereby be removed from the capillary. The porous part is inserted into a metal housing (=electrode) and electrical contact is established. A conductive liquid is flushed between porous capillary and metal housing in order to transport away gas bubbles that have formed, this being done by electrolysis of the aqueous buffer at the electrode. However, the porous part of the capillary can lead to a much higher surface adsorption of compounds, and this can result in substantial worsening of the analytical performance. The very shock-sensitive design of the treated capillary can also be disadvantageous.

A further known approach consists in the application of chip technology. In "Miniaturization of Analytical Systems", ISBN-10: 0-470-06110-3, page 237, A. Rios et al. describe solutions on microchips with integrated capillary electrophoresis which enable the voltage to be removed from the separation section before the detection.

In chip technology, the term separation capillary is replaced by micro separation channel, micro separation channels being introduced into the chip by etching processes.

The above publication presents a variant which has a side arm on a chip which departs from the actual separation channel, in which side arm the second contact electrode is also situated. Said side arm is coated with polyacrylamide in order to substantially reduce the electroosmotic flow. The separation channel made from glass, by contrast, is not coated, and so a higher EOF is achieved. Said difference in the EOF leads to an indirect hydrodynamic flow downstream of the bifurcation as far as the channel end. This flow is supported by an increase in the flow resistance in the side arm by virtue of the fact that the length of the side arm is larger than the distance from the bifurcation as far as the channel end. Mass spectrometry is described here as the detection technique. In the case of electrochemical detections, use is made of the term "off-channel detection" when the voltage is to be removed before the electrochemical detection. Several variants are presented with the aid of a decoupler in the above publication and by H. Chen et al. in *Trends in Analytical Chemistry*, Volume 26, No. 2, 2007.

J. S. Rossier et al., *Journal of Electroanalytical Chemistry*, 492 (2000), 15 describes a design in which microholes consisting of another polymer material are integrated at the end of the separation channel. This design allows the voltage to be removed from the separation channel before the electrochemical detection. Osbourne et al., *Analytical Chemistry*, 75 (2003), 2710, likewise describe a design with holes at the end of the separation channel. The holes are closed with a cellulose acetate membrane. The membrane is porous enough for electrical contact to be made with the electrode.

One object of the present invention is to provide a suitable capillary for capillary electrophoresis which enables the use of sensitive, nonoptical detectors such as, for example, mass-selective or electrochemical detectors, and minimizes the loss of analyte as far as possible (for example by irreversible immobilization).

Further objects of the present invention are to provide a suitable chemical separation and analysis device which includes the inventive capillary, and a chemical separation and analysis method with application of the inventive device.

In accordance with a first aspect of the present invention, this object is achieved by providing a plastic capillary tube for capillary electrophoresis, in which the plastic capillary tube has an inlet opening, an outlet opening and at least one hole in the capillary tube wall and the diameter of the hole on the inside of the capillary tube wall $d_{L(innen)}$ lies in the range from 0.5 μm to 30 μm.

As set forth above, the inventive capillary tube is a polymer or plastic capillary tube, that is to say a capillary tube made from a polymer material.

By contrast with the conventional glass capillary tubes, plastic capillary tubes exhibit fewer instances of surface adsorption for compounds with a strong tendency thereto because of their chemical structure. Examples are proteins and oligosaccharides. Electrophoretic separation in plastic capillary tubes is favourable for such classes of compound. Furthermore, chemically and mechanically stable plastic capillary tubes can be produced more cost-effectively.

As already discussed above, the use of sensitive and selective detectors presupposes that the voltage applied for the electrophoretic separation is removed as effectively as possible before the detector is reached. Within the scope of the present invention, this is enabled by virtue of the fact that the plastic capillary tube has at least one hole in the capillary tube wall and the diameter of the hole on the inside of the capillary tube wall $d_{L(innen)}$ lies in the range from 0.5 μm to 30 μm. The selected diameter of the hole in the capillary wall renders it possible, on the one hand, to remove the voltage but, on the other hand, the fluid is prevented as far as possible from escaping from the hole in the capillary tube wall for given test conditions.

BRIEF DESCRIPTION OF THE DRAWINGS

FIG. 1 is a schematic diagram of a chemical separation and analysis device.

DETAILED DESCRIPTION

The diameter of the hole on inside of the capillary tube wall $d_{L(innen)}$ preferably lies in the range from 1 μm to 20 μm, more preferably 2 μm to 12 μm.

In the case of a hole whose cross-sectional opening is not circular (for example elliptical), $d_{L(innen)}$ corresponds to the maximum diameter value.

The determination of the hole diameter can be performed, for example, via optical evaluation of optical microscope images. The diameter of the hole or bore is determined manually by inscribing circles via the 3-point method or by determining the centre and radius in the optical microscope image. The hole must be positioned centrally in this case.

In a preferred embodiment, the diameter of the hole is lesser on the inside of the capillary tube wall $d_{L(innen)}$ than the diameter of the hole on the outside of the capillary tube wall $d_{L(innen)}$.

In the case of a hole whose cross-sectional opening is not circular (for example elliptical), $d_{L(innen)}$ corresponds to the maximum diameter value.

The hole preferably has a conical shape. As is further explained below, such a conical shape of the hole can be implemented by laser action, for example, by laser drilling, that is to say "burning" a hole into the capillary wall.

The ratio of the hole diameter on the inside of the capillary tube wall to the hole diameter on the outside of the capillary tube wall $d_{L(innen)}/d_{L(außen)}$ preferably lies in the range from ½ to ⅐, more preferably ⅓ to ⅕. The ratio $d_{L(innen)}/d_{L(außen)}$ can be determined with the aid of a lateral optical micrograph of the capillary tube.

The axis of the hole preferably runs at an angle in the range of 90°±20°, more preferably in the range of 90°±10° to the longitudinal axis of the plastic capillary tube.

The inventive plastic capillary tube can have only one hole or, alternatively, two or more holes in the capillary tube wall.

In order as far as possible to minimize any loss of analyte or sample, it can be preferred for the plastic capillary tube to have only one hole in the capillary tube wall.

In so far as the plastic capillary tube has further holes in the capillary tube wall, it is possible with regard to the characteristics of said additional holes to refer to the above statements with regard to the first hole.

If the plastic capillary tube has two holes in the capillary tube wall, it is preferred that the two holes in the capillary tube wall lie as far as possible directly opposite one another, that is to say as far as possible lie on the same axis or are present uniaxially.

The dimensions of the inventive plastic capillary tube for capillary electrophoresis can be appropriately varied as a function of the sample to be examined, and of the optimal separation conditions.

The outside diameter of the plastic capillary tube $d_{K(außen)}$ preferably lies in the range from 50 μm to 200 μm, more preferably from 75 μm to 170 μm and the inside diameter of the plastic capillary tube $d_{K(innen)}$ preferably lies in the range from 10 μm to 150 μm, more preferably from 50 μm to 125 μm.

The thickness of the capillary tube wall preferably lies in the range from 1 μm to 25 μm.

The total length $L_0$ of the plastic capillary tube can vary depending on the nature of the sample to be analyzed and on the required separation conditions. A suitable total length $L_0$ of the plastic capillary tube can lie, for example, in the range from 40 cm to 150 cm, more preferably 55 cm to 100 cm.

Plastic capillary tubes with such dimensions are commercially available. The hole with a diameter which lies in the above-specified diameter range can be fitted in the capillary tube wall via methods which are known in principle to the person skilled in the art. Laser drilling can be named in this context, by way of example. A microchip laser with a wavelength of 532 nm, for example, can be used in laser drilling. The spot radiation technique, for example, is used. In this process, the laser beam is focused so as to produce a focal point on the capillary surface. Finally, the desired hole inside diameter can be fixed by varying irradiation parameters.

The inlet and outlet openings of the plastic capillary tube are preferably situated at its respective ends, that is to say that one end of the capillary tube has an inlet opening for accommodating the sample liquid, and the other end has an outlet opening.

The hole in the capillary tube wall is preferably situated as close as possible to the outlet opening of the tube. In a preferred embodiment, the hole is situated at a distance $L_1$ from that end of the capillary tube which has the outlet opening, and the total length of the plastic capillary tube is $L_0$ and the ratio $L_1/L_0$ lies in the range from 1/8 to 1/500, preferably 1/20 to 1/100.

By way of example, polyimide, polymethyl methacrylate, polycarbonate, polystyrene, polypropylene, polyether ether ketone, fluoropolymers, inter alia, and their mixtures may be named as suitable polymer materials from which the inventive plastic capillary tube can be made. It is also possible to add further substances, such as ceramic particles, to the polymer material in order, for example, to be able to influence the electroosmotic flow.

In accordance with a further aspect, the present invention provides a chemical separation and analysis device comprising a capillary electrophoresis unit which includes the above described inventive plastic capillary tube.

The outside of the capillary tube wall preferably makes contact in the region of the hole with an electrolytic liquid into which an electrode E1 dips.

The capillary electrophoresis unit preferably comprises a holding vessel for a sample or electrolyte liquid in the region of that end of the capillary tube which has the inlet opening, so that the liquid can easily be injected into the capillary tube, for example, by hydrodynamic or electrokinetic injection. It is preferred for an electrode E2 to be fitted in the region of the holding vessel so that it can dip into the sample or electrolyte liquid or make electrically conducting contact therewith in the case of a filled holding vessel.

The capillary electrophoresis unit preferably comprises a device element for building up an external pressure in the plastic capillary tube. This is possible for example by applying a gas pressure above the liquid. The liquid is led into the capillary at a different flow rate as a function of the external pressure. A further possibility consists in using a liquid-delivering pump. This is preferably positioned upstream of the voltage inlet.

In a preferred embodiment, the chemical separation and analysis device comprises a detection unit which is fitted downstream of the capillary electrophoresis unit.

The detection unit is preferably an electrochemical detector, mass selective detector, conductivity detector, SAW sensors (SAW: surface acoustic waves), impedance spectroscopy sensor or impedance sensor, optically based detectors, such as UV, VIS, fluorescence and refractive index detectors, or combinations of these detectors.

In accordance with a further aspect, the present invention provides a chemical separation and analysis method comprising the introduction of a sample liquid to be analyzed into the plastic capillary tube of the above-described inventive device, and the electrophoretic separation by application of a voltage.

The introduction of the sample liquid to be analyzed into the plastic capillary tube can be performed in a conventional way known to the person skilled in the art, for example, by hydrodynamically or electrokinetically conducted injection.

As already discussed above, it is preferred for the outside of the capillary tube to be in contact in the region of the hole with an electrolyte liquid or buffer liquid into which an electrode E1 dips or which is in electrically conductive contact with an electrode E1. For example, the capillary tube is guided in the region of the hole in the capillary wall through a container containing the electrolyte liquid or buffer liquid so that the outside of the tube makes contact in this region with the electrolyte liquid or buffer liquid. The electrode E1 can then also be admitted into said container. A further electrode E2 preferably dips into a sample liquid or is in electrically conductive contact therewith, the sample liquid being present in a vessel that is preferably positioned in the region of the inlet opening of the capillary tube. In this arrangement, the voltage across the hole in the tube wall is effectively removed from the capillary tube so that, after passing through the hole, the sample liquid is no longer subjected to voltage, and can therefore be fed to a downstream detection unit.

The sample liquid introduced into the plastic capillary tube is preferably subjected to a pressure in the range from 1 to 500 mbar, more preferably 5 mbar to 150 mbar.

The dwell time of the analyte in the region of the hole in the capillary tube wall can be minimized by exposing the sample liquid introduced into the plastic capillary tube to an external pressure. This also reduces the probability of small amounts of analyte diffusing out of the tube through the hole and migrating in the direction of the electrode E1. The effect of this external pressure is, moreover, that the analyte is moved on in the direction of the outlet opening after passing through the hole under the action of a hydrodynamic flow in the capillary tube.

After being guided past the hole in the capillary tube wall, the sample liquid is preferably fed to a downstream detection unit. As already stated above, the detection unit is preferably an electrochemical detector, mass-selective detector, conductivity detector, SAW sensors (SAW: Surface Acoustic Waves), impedance spectroscopy sensor or impedance sensor, optically based detectors, such as UV, VIS, fluorescence and refractive index detectors, or combinations of said detectors.

FIG. 1 shows a diagram of a preferred embodiment, which is described below in detail.

The preferred chemical separation and analysis device illustrated in FIG. 1 includes the above-described plastic capillary tube 1 with a hole 2 in the capillary tube wall. The end of the capillary tube having the inlet opening dips into a buffer liquid or electrolyte liquid or sample liquid 3. Also provided in said liquid is an electrode 4. A buffer vessel or electrolyte vessel 5 is placed at the hole 2 in the capillary tube wall. The second electrode 6 is provided in this buffer vessel or electrolyte vessel 5. A direct voltage (voltage between 1 and 30 kV) is applied between the electrodes. The voltage is led through the plastic capillary tube 1 between the capillary inlet opening and the hole 2 in the capillary tube wall, and closes the electric circuit. The electrophoretic separation takes place in this capillary segment. In order to put the sample into the capillary, the first buffer vessel or electrolyte vessel is exchanged with the sample vessel 3. The injection is carried out hydrodynamically or electrokinetically.

Depending on the analytical question involved, the polarity of the electrodes 4, 6 can be switched to negative-positive or vice versa. If negatively charged analytes are to be detected, the electrode in the first buffer vessel or electrolyte vessel 3 is a negative contact, and that in the second buffer vessel or electrolyte vessel 5 is a positive contact. In the electrophoretic separation section, the negatively charged analytes migrate to the positive pole, and are separated on the basis of their different mobility. A second electrophoretic effect is the electroosmotic flow EOF, already discussed above, which transports the entire bulk portion in the capillary tube in the direction of the positive pole. Consequently, when moving through the capillary tube 1, negatively charged analytes are accelerated and positively charged analytes are decelerated. By contrast, neutral particles migrate with the electroosmotic flow. Given that when use is made of the inventive capillary tube 1 the voltage is removed through the hole 2 in the capillary tube wall, the voltage is no longer applied after the hole 2. Consequently, the electroosmotic flow is changed into a hydrodynamic flow HDF. After the hole 2 in the capillary tube wall, the negatively charged analytes are situated outside the electrophoretic separation section and are led hydrodynamically to a downstream detector 7. In order to minimize the residence time of the analyte in the region of the hole 2, it is preferred for a hydrodynamic flow HDF to be applied to the capillary in addition to the voltage loading. The external pressure on the capillary is preferably ≤500 mbar and can be regarded as substitute for the EOF.

The invention is explained in more detail below with the aid of an example.

EXAMPLE

Use was made of a commercially available polyimide capillary tube with an outside diameter of 168 µm and an inside diameter of 122 µm. The wall thickness was therefore 23 µm. Such a plastic capillary tube is commercially available, for example from Goodfellow. The capillary tube had a total length of 60 cm. Two opposite holes were provided in the capillary tube wall at a distance of 7 cm from the capillary end having the outlet opening. This was performed by laser drilling using a microchip laser with a wavelength of 532 nm. The so-called spot irradiation technique was used, the laser beam being focused so as to produce a focal point on the capillary surface. The hole diameter was 10 µm on the inside of the capillary tube wall. The hole had a conical shape. The hole diameter at the outside of the wall was greater than the hole diameter at the inside of the wall.

As detection unit, use was made of a UV detector of Dionex with flow cuvette which was connected to the plastic capillary tube via a transfer line. A commercially available aqueous borate solution was used as buffer. Nitrate was used as UV-active test substance.

A voltage of U=15 kV was applied. Furthermore, an external pressure of 4 psi was applied. A current of 55 µA flows at the position of the two holes in the capillary tube wall. The current flow is interrupted at other positions in the capillary. Furthermore, despite an external pressure of 4 psi there is no indication of drop formation owing to escaping buffer liquid from the holes in the capillary wall. The example shows that voltage can escape at the position of the holes in the capillary wall but that, in contrast, the buffer liquid is held back in the capillary tube at a given pressure.

As already mentioned above, nitrate was injected as analyte. For a voltage of U=−15 kV and, in addition, a hydrodynamic pressure of 4 psi, the electropherogram returned a retention time of 2.3 min for the nitrate.

As discussed above, the inventive plastic capillary tube and the inventive chemical separation and analysis device including this capillary tube can be used to implement the following advantages, inter alia:

By comparison with glass capillaries, the surface charges in plastic capillary tubes are substantially reduced. The positive effect of this is that large charged molecules (in particular biomolecules) are not adsorbed by the surface charges and can be separated electrophoretically.

Fastening of detectors which come into contact with the buffer liquid. The voltage for the electrophoretic separation can be removed through the hole provided in the capillary tube wall, without the detectors being negatively influenced thereby.

Detection sensitivity is retained, no sheath liquid is used. The sample (injection amount) is not diluted.

Owing to the given design, the formation of gas by electrolysis of the buffer does not affect the electrophoretic operation.

The invention claimed is:

1. Chemical separation and analysis device for an analyte comprising a capillary electrophoresis unit which includes a plastic capillary tube having an inlet opening and an outlet opening and, furthermore, has at least one hole in the capillary tube wall and the diameter of the hole on the inside of the capillary tube wall $d_{L(innen)}$ lies in the range from 0.5 µm to 30 µm and is smaller than the diameter of the hole on the outside of the capillary tube wall $d_{L(außen)}$, the ratio of $d_{L(innen)}$ to $d_{L(außen)}$ being in the range from ½ to ⅐.

2. Chemical separation and analysis device according to claim 1, in which the hole has a conical shape.

3. Chemical separation and analysis device according to claim 1, in which the outside diameter of the plastic capillary tube $d_{K(außen)}$ lies in the range from 50 µm to 200 µm, and/or the inside diameter of the plastic capillary tube $d_{K(innen)}$ lies in the range from 10 µm to 150 µm.

4. Chemical separation and analysis device according to claim 1, in which the hole in the capillary tube wall is situated at a distance $L_1$ from the end of the plastic capillary tube which has the outlet opening, the total length of the plastic capillary tube is $L_0$, and the ratio $L_1/L_0$ lies in the range from ⅛ to 1/500.

5. Chemical separation and analysis device to claim 1, in which the plastic capillary tube is made from polyimide, polymethyl methacrylate, polycarbonate, polystyrene, polypropylene, polyether ether ketone, fluoropolymer, or their mixtures.

6. Chemical separation and analysis device according to claim 1, in which the outside of the capillary tube wall makes contact in the region of the hole with an electrolytic liquid into which an electrode E1 dips.

7. Chemical separation and analysis device according to claim 1, in which the capillary electrophoresis unit has a device element for building up of an external pressure in the plastic capillary tube.

8. Chemical separation and analysis device according to claim 1, in which the chemical separation and analysis device comprises a detection unit which is located downstream of the capillary electrophoresis unit.

9. Chemical separation and analysis method comprising the introduction of a sample liquid to be analyzed into the plastic capillary tube of the device according to claim 1, and electrophoretic separation of the sample by application of a voltage.

10. Method according to claim 9, in which the sample liquid introduced into the plastic capillary tube is subjected to pressure in the range from 1 to 500 mbar.

11. Method according to claim 9, in which the sample liquid is fed to a detection unit after passing through the capillary electrophoresis unit.

* * * * *